United States Patent [19]
Grabner

[11] Patent Number: 5,176,449
[45] Date of Patent: Jan. 5, 1993

[54] METHOD AND ARRANGEMENT FOR MEASURING THE FLASH POINT OF LIQUIDS AND SOLIDS

[76] Inventor: Werner Grabner, Nussdorferstrasse 4/11, A- 1090 Vienna, Austria

[21] Appl. No.: 795,044

[22] Filed: Nov. 20, 1991

[30] Foreign Application Priority Data

Nov. 23, 1990 [AT] Austria .................. 2382/90

[51] Int. Cl.$^5$ .................. G01K 11/00; G01N 25/52
[52] U.S. Cl. .................. 374/8; 73/36; 374/157
[58] Field of Search .................. 374/8, 157; 73/36

[56] References Cited

U.S. PATENT DOCUMENTS

| | | | |
|---|---|---|---|
| 4,140,004 | 2/1979 | Smith et al. .................. | 73/36 X |
| 4,348,117 | 9/1982 | Michels .................. | 374/24 |
| 5,052,817 | 10/1991 | Bement et al. .................. | 374/8 |

FOREIGN PATENT DOCUMENTS 1004778  3/1983  U.S.S.R. .................. 374/8

Primary Examiner—Daniel M. Yasich
Attorney, Agent, or Firm—Steinberg & Raskin

[57] ABSTRACT

The present invention is related to a device and method for determining the flash point of a liquid or solid material to be tested by measuring the pressure obtained in the measuring chamber after an ignition. According to the invention, a liquid or solid is placed into a measuring vessel and the measuring vessel is heated. The measuring vessel is tightly closed with a cover. At a given temperature the generated vapor-air-mixture is ignited and the pressure increase occurring due to the temperature increase is taken as a measure for the size of the flame for determining the flash point. The pressure increase is preferably measured with a piezoresistive pressure transducer. The temperature of the heated cover is measured with the temperature sensor and the sample temperature with the temperature sensor.

7 Claims, 1 Drawing Sheet

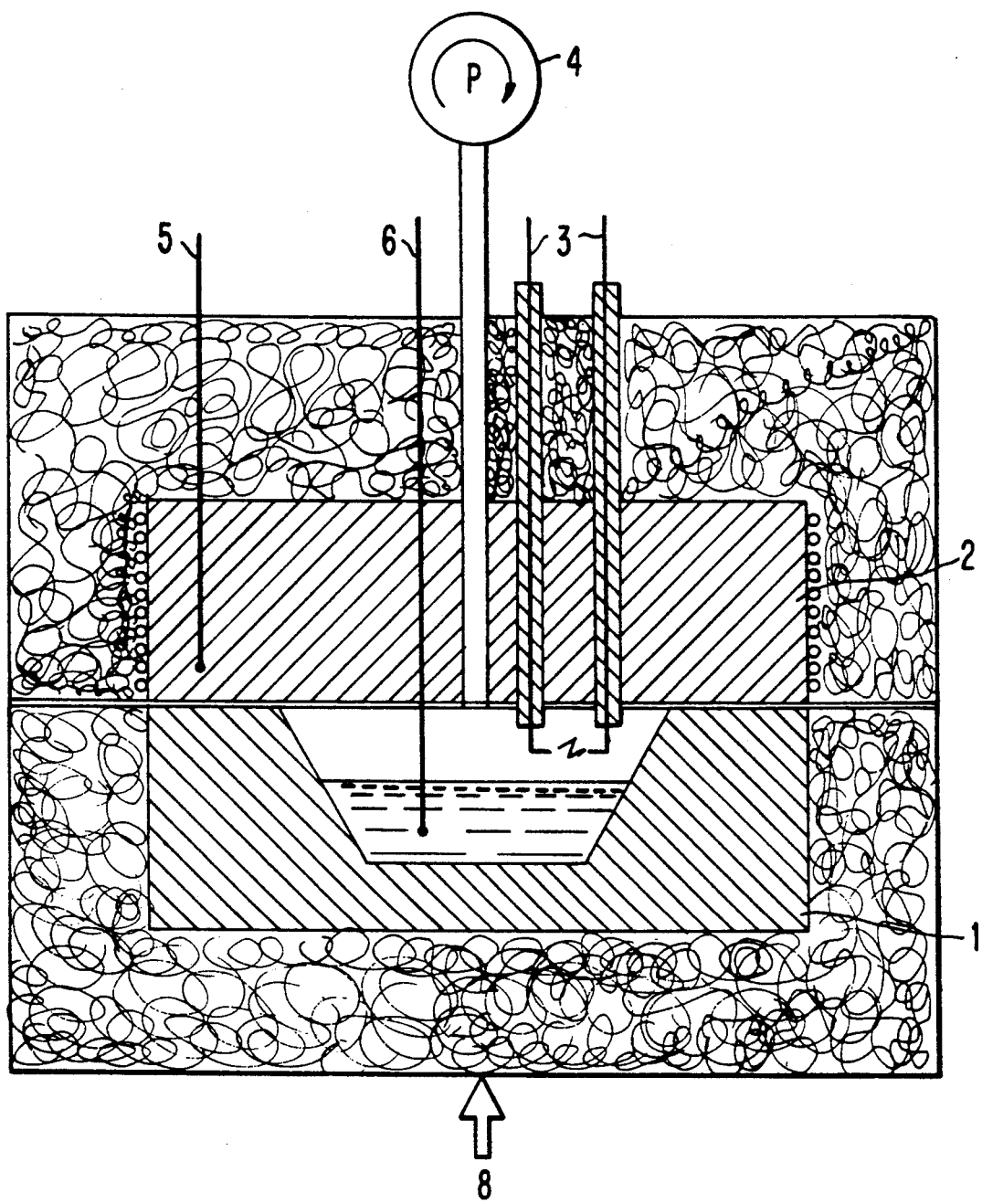

METHOD AND ARRANGEMENT FOR MEASURING THE FLASH POINT OF LIQUIDS AND SOLIDS

FIELD OF THE INVENTION

The present invention relates to a method and an arrangement for measuring that temperature at which, under laboratory conditions, the vapor of a given substance forms with the air a flammable mixture.

BACKGROUND OF THE INVENTION

The flash point of a substance is used in connection with transport and safety regulations in order to define flammable and explosive materials. The flash point can also give information about the presence of readily volatile and flammable components in substances of low volatility and flammability.

Several internationally recognized measuring methods, recognized by ASTM and ISO, exist for measuring the flash point. The definition of flash point according to ASTM is the point of lowest temperature, corrected to the barometric air pressure of 101.3 kPa at which through application of a test flame the vapor of the sample ignites. Igniting is defined as a flame which by itself wanders over the surface of the sample and covers at least two thirds of the surface.

In principle, these methods always involve a sample vessel which is heated with a flame or electrically. The vessel is either open or closed. The open design is rarely still permitted for test measurements since the volatile components give off vapors and can no longer contribute to the combustion.

All test arrangements with closed vessels have in common the method of heating the vessel from the vessel. Thereby the temperature of the cover always lags behind so that condensation phenomena and flash point increases connected therewith occur.

Ignition of the mixture takes place by dipping an ignition flame, an incandescent filament or an electric spark into an opening of the cover.

From DDR-P 124 682 it is known to irradiate a sample vessel in a chamber with a floor, wall, and ceiling heating system wherein to avoid local overheating of the vessel, the three heating groups are appropriately power-controlled. Such power regulations are problematic and the measurement itself is complicated.

Reference is also made to my U.S. Pat. No. 4,901,559, hereby incorporated by reference, which is directed to a method for measuring vapor pressure of liquids in a previously-evacuated measuring cell, and influence of the gas dissolved in the liquid on the measuring results is eliminated.

The detection of a flash point takes place either manually through optical observation through the ignition opening or automatically via temperature measurements (temperature rise due to combustion) or an ionization measurement (changes of the ionization state of the gas due to combustion). The disadvantage of this detection in the case of manual observation is the subjective judgement of the flame size. Automatic detection through heat or ionization provides poor reproducibility since the flame size can rarely be determined.

SUMMARY OF THE INVENTION

It is therefore an object of the present invention to create a method for measuring the flash point which can be automated, is well suited for commercial use and which therein supplies precise and reproducible measuring results.

A further object of the invention is to create also an arrangement which permits a sample carrying-out of the method according to the invention and to achieve high measuring accuracy and good reproducibility.

Pursuant to the method according to the invention, the substance to be tested is placed into a sample cup and the sample cup is pressed onto the cover. The determination of an ignition for determining the flash point is carried out by measuring the pressure obtained in the measuring chamber after an ignition. The pressure increases in the measuring chamber with an ignition of the substance to be tested through the temperature increase brought about by the flame. Thereby a further object of the invention is achieved, i.e., that the temperature of the cover is always greater than that of the sample cup in which is disposed the substance to be measured. Condensations and the changes of the flash point connected therewith are thereby excluded.

BRIEF DESCRIPTION OF THE DRAWING

The following drawing is illustrative of an embodiment of the invention and is not meant to limit the scope of the invention as encompassed by the claims.

FIG. 1 is a cross-sectional view of a preferred embodiment of the present invention.

DETAILED DESCRIPTION

Referring to the apparatus shown in FIG. 1, the cover 2 and the sample cup 1 are preferably fabricated of aluminum for the purpose of good heat conduction. Heating the cover 2 preferably takes place with an electrical heating system. The temperature measurement and regulation takes place via temperature sensor 5 thermally well coupled with the cover. The temperature of the heated cover is measured with the temperature sensor 5.

Two electrodes 3 are fixedly installed in the heated cover for the electrical ignition. The electrodes are electrically insulated. The ignition points of the electrodes are disposed approximately 2 mm above the surface of the substance to be measured. The ignition spark is generated with a commercially available ignition coil.

A temperature sensor 6 is also installed in the cover which projects directly into the substance S to be measured. Therewith the temperature of the substance to be measured is detected precisely and is used subsequently as a measured value for the flash point.

As previously stated, an important aspect of the present invention is the detection of the flash point. It is assumed that each combustion is connected with an increase in temperature. However, in contrast to the conventionally applied temperature measurements, the present invention utilizes the pressure increase due to the combustion temperature within the measuring chamber to make this determination.

By means of the method according to the present invention, the above stated goal can very readily be met and it is an essential advantage of this method that the measured pressure increase is not a function of the temperature of the burned gas but rather also of the volume of the flame. Thereby, by setting a threshold for the pressure increase, the size of the flame in terms of volume can be detected.

For example, if a combustion temperature of approximately 1000° C. is assumed, then the pressure at the same volume increases according to the gas equation.

$p*v/T = $ constant $p2/p1 = T2/T1$ $p2 = $ pressure at 1000° C.

$p1 = $ pressure at the measuring temperature (101.3 kPa)

$T2 = $ absolute combustion temperature $(1000 + 273)$ $T1 = $ absolute measuring temperature $(tm + 273)$ At a measuring temperature of 100° C. this corresponds to a pressure increase of approximately 350.0° kPa.

The given volume or burned gas with high pressure is distributed over the entire gas volume in the measuring chamber. Therefrom the actual pressure increase in the chamber can be determined. A correction of the required pressure increase over the measuring temperature is possible in a simple manner and is also required for the precise determination.

Under the assumption that the flame occupies 20% of the free gas volume, a final pressure increase of approximately 50 kPa results. This is a measured value which can be measured with great accuracy.

For the precise detection of the pressure increase preferably a piezoresistive pressure transducer is preferably used which is connected via a tube line with the measuring chamber.

EXAMPLE—MEASURING PROCESS

The substance to be measured, primarily a liquid, is placed into the sample cup 1 in a given quantity. The sample cup 1 is pressed either manually or automatically by means of pressing device 8 against the heatable cover 2, forming a closed measuring chamber. Sealing of the measuring chamber is achieved by metal contact of the sample cup 1 and the cover 2.

The measuring process is started thereby that the cover 2 is heated to a given temperature which with certainty is below the expected flash point temperature. Monitoring and measuring the temperature takes place via the temperature sensor 6. Through the thermal contact of the sample cup 1 with the cover 2 the temperature of the substance can be measured.

After a waiting period for the temperature adaptation of the sample cup 1 to the cover 2, the temperature of the cover 2 is slowly increased further and at constant temperature intervals an ignition via the electrodes 3 is carried out.

Immediately after the ignition, the pressure increase in the measuring chamber is measured via the measuring instrument 4 which is implemented preferably as piezoelectric pressure transducer. The measuring chamber is defined by the sample cup 1 or the volume of the substance to be measured and the free space under the cover, respectively.

The examples provided above are not meant to be exclusive. Many other variations of the present invention would be obvious to those skilled in the art, and are contemplated to be within the scope of the appended claims.

What is claimed is:

1. A method for measuring the flash point of liquids and solids, comprising placing a sample to be tested into a sample cup, pressing said sample cup onto a cover, thereby forming a closed heatable measuring chamber, heating said sample in said closed measuring chamber by heating said cover such that a flammable vapor is produced from said sample, causing an ignition of said flammable vapor in said measuring chamber, said ignition causing an increase in presence in said measuring chamber, determining the flash point of said sample by measuring said increase in pressure obtained in said measuring chamber after the ignition.

2. The method of claim 1, further comprising heating said cover such that the temperature of said sample to be tested is always lower than the temperature of said cover.

3. The method of claim 1, further comprising heating said cover at constant temperature intervals.

4. An arrangement for measuring the flash point of liquids and solids, comprising a measuring chamber including a sample cup adapted to contain a sample to be tested and a heatable cover, said sample cup located below said cover, an electrical ignition arrangement for igniting the sample, a temperature measuring device for measuring and regulating the temperature of said cover, a pressing device adapted to press said sample cup from below against the cover such that said sample cup is heated by said cover, the temperature of the sample cup and the sample being lower than the temperature of said cover, a pressure measuring device for measuring the increase in pressure in said measuring chamber when the sample is ignited, the flash point of the sample being derived from the measured increase in pressure in said measuring chamber when the sample is ignited.

5. The arrangement of claim 4, wherein said electrical ignition arrangement, said pressure measuring device, and said temperature measuring device are disposed in said heatable cover, said sample cup being adapted to be removed from said cover for emptying, cleaning and filling.

6. The arrangement of claim 5, wherein said pressure measuring device is a piezoelectrical pressure transducer.

7. An arrangement for measuring the flash point of liquids and solids comprising a sample cup filled with the sample to be tested, a heatable cover pressed firmly to said cup, forming a metal sealed closed measuring chamber, a pressing device adapted to press said sample cup from below against said cover, a heating device arranged in said cover such that said sample cup is heated by said cover and the temperature of the sample cup is lower than the temperature of said cover, an electrical ignition arrangement for the ignition of the flammable vapor from the sample, a first temperature sensor for measuring and regulating the temperature of said cover, a second temperature sensor for regulating and measuring the temperature of said sample, a pressure measuring device for measuring the increase in pressure in said measuring chamber when the sample is ignited, the flash point of the sample being derived from the measured increase in pressure in said measuring chamber when the sample is ignited.

* * * * *